(12) United States Patent
Besson

(10) Patent No.: US 6,411,670 B1
(45) Date of Patent: Jun. 25, 2002

(54) DATA REBINNING TO INCREASE RESOLUTION IN CT IMAGE RECONSTRUCTION

(75) Inventor: Guy M. Besson, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/437,430

(22) Filed: Nov. 17, 1999

(51) Int. Cl.[7] .................................................. A61B 6/03
(52) U.S. Cl. ........................................... 378/4; 378/901
(58) Field of Search ................................ 378/4, 15, 19, 378/901

(56) References Cited

U.S. PATENT DOCUMENTS

| | | |
|---|---|---|
| 4,894,775 A * | 1/1990 | Kritchman et al. ............. 378/4 |
| 5,208,746 A | 5/1993 | King et al. |
| 5,216,601 A | 6/1993 | Crawford et al. |
| 5,257,183 A | 10/1993 | Tam |
| 5,446,776 A | 8/1995 | Tam |
| 5,559,846 A | 9/1996 | Tam |
| 5,594,766 A | 1/1997 | Tam |
| 6,108,575 A | 8/2000 | Besson |
| 6,163,617 A * | 12/2000 | Heuscher et al. ........... 382/132 |
| 6,173,032 B1 | 1/2001 | Besson |

OTHER PUBLICATIONS

Besson, "New classes of helical weighting algorithms with applications to fast CT reconstruction," Med. Phys. 25(8), Aug. 1998, pp. 1521–1531.

Henson et al., "Multilevel Image Reconstruction with Natural Pixels," Jul. 5, 1994 (accessed May 27, 1999), pages printed from the Internet starting at http://www.cecm.sfu.ca/~malimber/breck/breck.html on May 27, 1999.

* cited by examiner

*Primary Examiner*—David V. Bruce
(74) *Attorney, Agent, or Firm*—Carl B. Horton, Esq; Armstrong Teasdale LLP

(57) ABSTRACT

The present invention, in one aspect, is a method for producing an enhanced tomographic image of an object. The method includes steps of obtaining fan beam projection data of the object from a tomographic scan; rebinning the fan beam projection data into a quantity of parallel projection data points; applying interpolation to the quantity of parallel projection data points to increase the quantity of parallel projection data points; and generating a tomographic image from the increased quantity of parallel projection data points.

26 Claims, 8 Drawing Sheets

$Z = Z(\theta=O) + \gamma \times (\Delta Zr/2\pi) = Z(\theta=O) + (\Delta Zr/2\pi) \times \arcsin(r/S)$

DATA REBINNING TO INCREASE RESOLUTION IN CT IMAGE RECONSTRUCTION

BACKGROUND OF THE INVENTION

This invention relates generally to computed tomography (CT) imaging and, more particularly, to reconstructing an image from CT scan data.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical scan" is performed. To perform a "helical" scan, the patient is moved while the data for the prescribed number of slices is acquired. Such a system generates a single helix from a one fan beam helical scan. The helix mapped out by the fan beam yields projection data from which images in each prescribed slice are reconstructed.

Although fan-beam data may be acquired more efficiently than parallel beam data, the theory of imaging reconstruction was first developed for parallel data. In multislice fan-beam CT scanners, four variables are key in describing projection sampling. They are source angle $\beta$ (and the source angle increment between two views, $\Delta\beta$), fan angle $\gamma$ (and the fan angle increment between two rays, $\Delta\gamma$), individual slice aperture $\Delta Zs$, and pitch $p=\Delta Zr/\Delta Zs$, relating a table advance $\Delta Zr$ per 360° rotation to $\Delta Zs$. In practical scanning, often variable increments $\Delta\beta$, $\Delta\gamma$, $\Delta Zs$, and p are determined to optimize a scanning parameter, for example, coverage in a given amount of time, and are not well matched, or more specifically, sampling is not well balanced. In the coverage optimized case, $\Delta\beta>>\Delta\gamma$, and azimuthal resolution does not match radial resolution. Decreasing view sampling time to reduce $\Delta\beta$ requires very expensive and pervasive system design changes, including changes to the data acquisition system (DAS), slip ring and reconstruction system. In other situations, it is possible to increase scanning time, for example, in head imaging, where patient immobilization is easy to achieve. It is then possible to obtain $\Delta\beta<\Delta\gamma$, while directly reducing $\Delta\gamma$ would require expensive and complex system design changes, such as reducing detector cell pitch and increasing a number of detector cells, or enabling focal spot wobbling. Moreover, in helical scanning, the quality of the reconstructed image is affected by pitch size, that is, the distance through which the object is moved relative to the z-axis as the gantry rotates 360 degrees. Frequently, to reduce total scan time, either pitch size or slice collimation is increased. As a consequence, the quality of the reconstructed image is reduced.

Rebinning data from fan-beam to parallel would fully leverage all data in a scan, or of a portion of a scan. For instance, two or more "conjugate rays" that provide a measurement of a given line integral in an axial scan comprising 360° or more of projection data could be combined to effectively decrease $\Delta\gamma$ by a factor 2 to $\Delta\gamma/2$ via what is known in the art as "quarter offset." Further, as a given, rebinned, i.e., not measured directly, Radon space sample corresponds to a line integral through a patient, estimation of such Radon space samples in theory requires knowledge of all scan projection data, or of portions of scan projection data sufficient to reconstruct an image though a slice of interest. This requirement comes about because reconstruction of a single pixel value involves all such projection data. Accordingly, rebinning the data from fan-beam to parallel provides leveraging of a higher resolution available along one sample direction to increase an effective resolution along another sampling direction, and therefore remedies scan acquisition sampling limitations along the latter direction. Although this leveraging is described below in terms of partial differential equations, it can as well be understood from spectral considerations for a band-limited or quasi-band-limited function, such as a slice of interest in computed tomography. Indeed, the sampling theorem indicates that, providing a 2D or 3D sampling density is sufficient, undersampling in one direction can be compensated by finer sampling along the other directions. Gridding methods may be effectively applied to regrid the samples on a uniformly sampled set of estimates. Similarly, it is well known in the art that sampling a function and its first derivative simultaneously effectively allows doubling of a sample interval and recovery of an original function.

It would therefore be desirable to provide a method for rebinning fan data into parallel data for improved image reconstruction. It would also be desirable to obtain and utilize additional information in each scan to increase the quality of the reconstructed images. In addition, it would be desirable to provide methods for obtaining such additional information from nonuniformly sampled projection data. It also would be desirable to provide a method for increasing resolution that provides for increased helical scanning coverage in a given amount of time without degradation of image quality.

BRIEF SUMMARY OF THE INVENTION

There is thus provided, in one embodiment of the present invention, a method for producing an enhanced tomographic image of an object. The method includes steps of obtaining fan beam projection data of the object from a tomographic scan; rebinning the fan beam projection data into a quantity of parallel projection data points; applying interpolation to the quantity of parallel projection data points to increase the quantity of parallel projection data points; and generating a tomographic image from the increased quantity of parallel projection data points.

The methods and apparatus of the present invention provide rebinning fan data into parallel data for improved image reconstruction. Additional information is obtained and utilized in each scan to increase the quality of the reconstructed images. The additional information can be obtained and used even in the case of nonuniformly sampled projection data. The methods and apparatus of the present invention also provide increased helical speed coverage by using thicker slice collimation, without degradation of image quality, and increased volume coverage while maintaining z-resolution in a reconstructed slice.

DETAILED DESCRIPTION OF THE INVENTION

Figure 1:
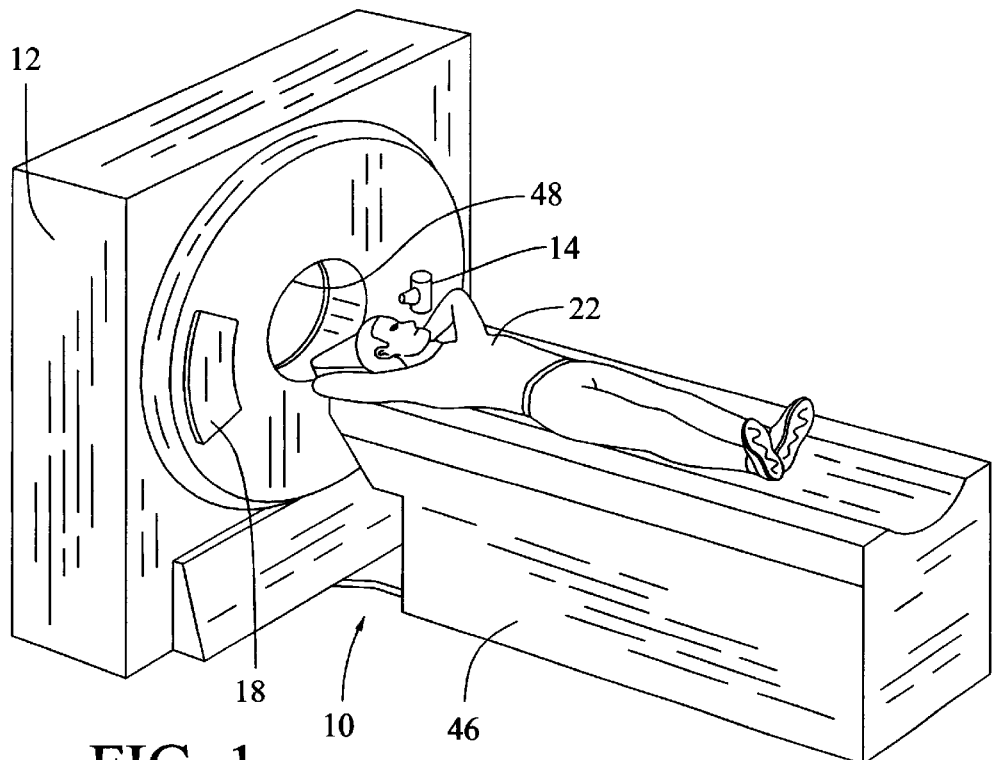
FIG. 1 is a pictorial view of a CT imaging system.
Figure 2:
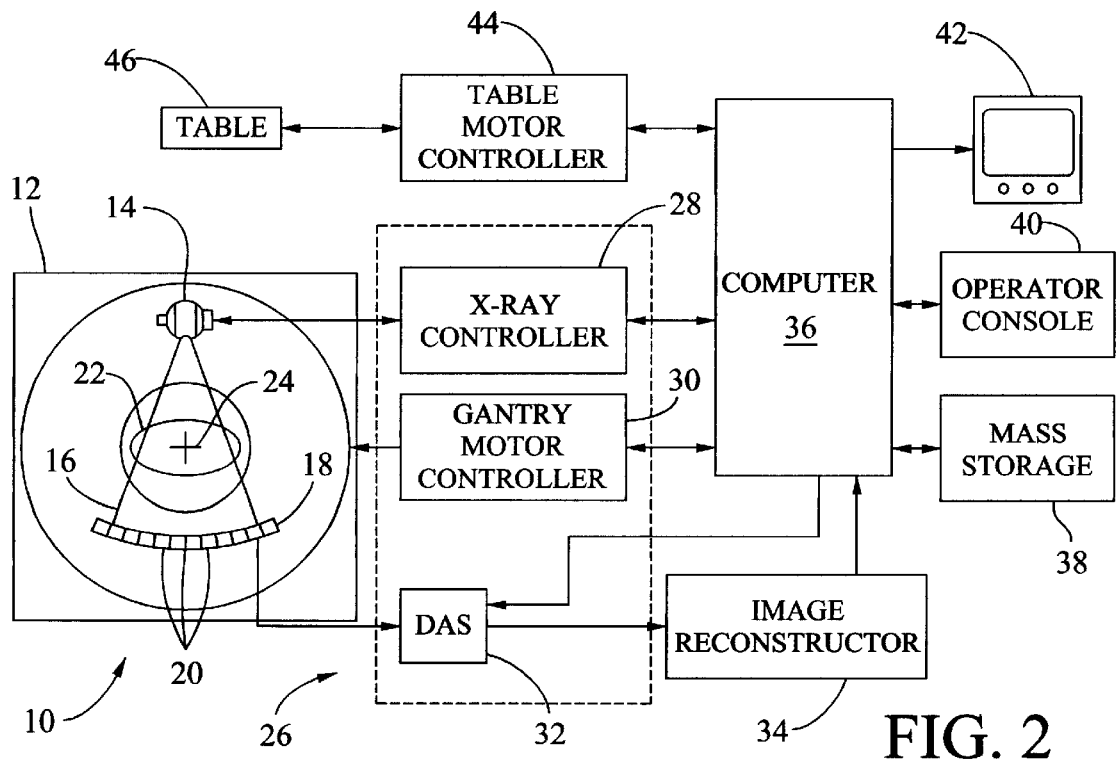
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
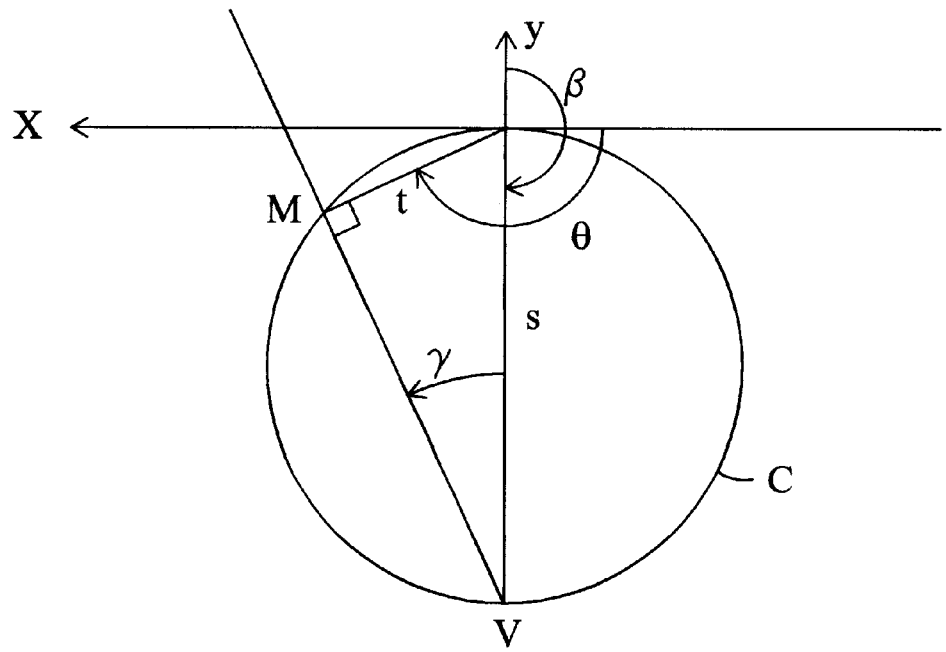
FIG. 3 is a geometric representation of a fan beam of a multislice CT scanner illustrating an associated Radon space sampling.

In one embodiment of the invention and referring to FIG. 3, fan beam projection data is obtained of object or patient 22. In the geometric representation of a fan beam of a multislice CT scanner 10 shown in FIG. 3, x and y are geometric axes, O is an isocenter of the scanner, V is a vertex of a radiation source, P is a single sample point in Radon space, and t is a distance coordinate. Angles $\beta$, $\theta$, and $\gamma$ are measured as shown, with all angles illustrated in this view being positive. A z-axis of the scanner is perpendicular to both the x- and y-axes, and is directed into the plane of the figure. Circle C represents a locus of potential samples that can be acquired at vertex position V. Only points on C up to a maximum angle $|\gamma| \leq \Gamma = \gamma\max$ (not shown in FIG. 3) are actually acquired in any given scan.

Let $p(\beta, \gamma, k)$ denote fan beam data acquired by multislice CT scanner 10 at projection angle $\beta$, ray angle (fan-angle) $\gamma$, and row (slice) index k. A density function (image) to be reconstructed is denoted by $f$ while $Rf$ represents the Radon transform of $f$ (projection data). Accordingly, $$p(\beta, \gamma, k) = Rf(\theta, t, z) \tag{1}$$

where $\theta = \beta + \gamma$, $t = S \sin(\gamma)$; and $z = z_o + kx\Delta Zs +$ $$z = z_0 + kx\Delta Zs + \left(\frac{\beta}{2\pi}\right)x\Delta Zr;$$

and $\Delta Zs$ is a slice aperture and $\Delta Zr$ is a table advance per $2\pi$ rotation.

Thus, the following differential equations are written:

$$\frac{\partial p}{\partial \beta} = \frac{\partial Rf}{\partial \theta}\frac{\partial \theta}{\partial \beta} + \frac{\partial Rf}{\partial t}\frac{\partial t}{\partial \beta} + \frac{\partial Rf}{\partial z}\frac{\partial z}{\partial \beta} \tag{2}$$

$$\frac{\partial p}{\partial \gamma} = \frac{\partial Rf}{\partial \theta}\frac{\partial \theta}{\partial \gamma} + \frac{\partial Rf}{\partial t}\frac{\partial t}{\partial \gamma} + \frac{\partial Rf}{\partial z}\frac{\partial z}{\partial \gamma} \tag{3}$$

-continued $$\frac{\partial p}{\partial k} = \frac{\partial Rf}{\partial \theta}\frac{\partial \theta}{\partial k} + \frac{\partial Rf}{\partial t}\frac{\partial t}{\partial k} + \frac{\partial Rf}{\partial z}\frac{\partial z}{\partial k} \quad (4)$$

which are written in matrix form as:

$$\begin{bmatrix} \frac{\partial p}{\partial \beta} \\ \frac{\partial p}{\partial \gamma} \\ \frac{\partial p}{\partial k} \end{bmatrix} = \begin{bmatrix} 1 & 0 & \frac{\Delta Zr}{2\pi} \\ 1 & S\cos(\gamma) & 0 \\ 0 & 0 & \Delta Zs \end{bmatrix} \begin{bmatrix} \frac{\partial Rf}{\partial \theta} \\ \frac{\partial Rf}{\partial t} \\ \frac{\partial Rf}{\partial z} \end{bmatrix} \quad (5)$$

The inverse is determined as:

$$\begin{bmatrix} \frac{\partial Rf}{\partial \theta} \\ \frac{\partial Rf}{\partial t} \\ \frac{\partial Rf}{\partial z} \end{bmatrix} = \begin{bmatrix} 1 & 0 & \frac{-\Delta Zr}{2\pi \Delta Zs} \\ \frac{-1}{S\cos(\gamma)} & \frac{1}{S\cos(\gamma)} & \frac{\Delta Zr}{2\pi S\cos(\gamma)\Delta Zs} \\ 0 & 0 & \frac{1}{\Delta Zs} \end{bmatrix} \begin{bmatrix} \frac{\partial p}{\partial \beta} \\ \frac{\partial p}{\partial \gamma} \\ \frac{\partial p}{\partial k} \end{bmatrix} \quad (6)$$

Accordingly, $$\frac{\partial Rf}{\partial \theta} = \frac{\partial p}{\partial \beta} - \frac{1}{2\pi}\frac{\Delta Zr}{\Delta Zs}\frac{\partial p}{\partial k}; \quad (7)$$

$$\frac{\partial Rf}{\partial t} = \frac{1}{S\cos(\gamma)}\left\{\frac{\partial p}{\partial \gamma} - \frac{\partial p}{\partial \beta} + \frac{1}{2\pi}\frac{\Delta Zr}{\Delta Zs}\frac{\partial p}{\partial k}\right\}; \text{ and}$$

$$\frac{\partial Rf}{\partial z} = \frac{1}{\Delta Zs}\frac{\partial p}{\partial k}.$$

In one embodiment of the invention, derivative data derived from Equations (7) are used to increase resolution in a helical CT scan. To understand how the data are used, it is necessary to understand how a scan acquires a linear attenuation distribution function of voxels within object 22. It is also necessary to understand how interpolation can be used to improve image quality and how derivative information can be obtained and applied, in accordance with the sampling theorem, in such interpolation.

Consider a voxel at fixed (x,y,z). In an axial scan (at z fixed), the reconstructed linear attenuation distribution $f(x,y,z)$ can be considered as a function of P projections (views) acquired during the scan. P here varies depending on the reconstruction method used: segmented, underscan, overscan, or standard. Let $d_i$ be a weighted, filtered, and γ-interpolated projection value corresponding to the backprojection ray passing through (x,y,z) and associated with view $v_i$. Then $f$ is written as:

$$f(x, y, z) = f_{x,y,z}(d_1, \ldots, d_P) \quad (8)$$

where the dependency on $d_i$ is through a backprojection operator BP(.).

In a helical scan at a known (possibly variable) table 46 velocity, consider backprojection rays passing through a line parallel to the z-axis determined by a given point pixel at point $(x_o,y_o)$. For any given ray angle through $(x_o,y_o)$ (in a plane orthogonal to z), a collection of rays indexed by (i,k) pass through an associated line z->$(x_o,y_o,z)$. Associated projection data are $p_{i,k} = p[\beta_i, z_k, \gamma(x_o,y_o,\beta_i)]$. For a fixed projection angle i, samples for subset $p_{i)k}$, k=1, ..., V are usually equispaced in z, as they correspond to various slices (rows) of the detector (and these rows are typically equispaced). However, when combining several projections (views corresponding to different indicies i), and in particular, when combining samples from two conjugate views, resulting samples are not, in general, equidistant in z. Indeed, even when a pitch of a multislice scanner is chosen such that, for $(x_o,y_o)=(0,0)$ (i.e., γ=0), the conjugate rays exactly interlace (as is the case at pitch 3:1 on a four slice scanner). For other pixels $(x_o,y_o) \neq (0,0)$, exact interlacing no longer applies and resulting set samples are not equispaced in z. For a given $z_o$, an attenuation value reconstructed at $(x,y,z_o)$ is a function of weighted, filtered, and interpolated projection values $\{d_{i,k}\}$. The nature of the function depends on the particular type of helical reconstruction algorithm considered and a type of scanner 10 used, for example, single-slice or multislice. For instance, in one embodiment for high z-resolution in cases in which at least two conjugate samples of a given ray are available, z-interpolation weights take into account closest rays (in z) that belong to conjugate projections. In another embodiment, for high-speed coverage in cases in which conjugate samples are not available, helical synthesizing interpolates and/or extrapolates from the $(p_i)_k$, k=1, ..., V at i fixed. Optimal reconstruction is obtained by combining all $p_{i,k}$ and estimating $d_i(z_o)$ from the full data set. Estimates $d_i(z_o)$ are then filtered and backprojected using the same backprojection operator BP(.) used in the axial case.

When an original distribution $f(x,y,z)$ to be reconstructed is band-limited along z to [−B,B] in frequency, and samples used for interpolation (a subset of $\{d_{i,k}\}$) are equidistant in z, the sampling theorem assures that an exact interpolation can be obtained from an infinite set of samples $\{\{d_{i,k}\}_k$, provided the sampling interval Dz satisfies the Nyquist criterion: Dz≦1/(2B). It follows from the theory of linear systems that availability of derivative information aids the interpolation. More specifically, when samples of the outputs $y_1(u), \ldots, y_m(u)$ of M linear and shift-invariant systems $H_1(w), \ldots, H_M(w)$ driven by x(u) are available, where w designates a frequency variable, and u is an independent variable (time or space), then the sampling interval can be increased from 1/(2B) to M/(2B), while still allowing recovery of the original function.

In the case of helical image reconstruction, samples of a line-integral function l(z) are of interest. Differential operator D(l)=l' is linear and shift-invariant. Therefore availability of derivative information l'(z) allows, in theory, for the sampling interval, which is directly related to pitch, to be increased by a factor of 2. In practice, however, samples $\{d_{i,k}\}$ are not necessarily equispaced, such as in the fan-beam case.

For a given helical reconstruction method and a given reconstruction plane location $z_o$, i.e., given weighting, filtering, x- and z-interpolation functions, a set of samples $\{d_{i,j,k}\}$ is obtained by applying the weighting ($W_{i,k,zo}$), filtering, ($F_j$), and γ-interpolation linear operators to samples of line-integral function $\{l_{i,j,k}\}$: $\{d_{i,j,zo}\}=F_1(W_{i,k,zo}(\{l_{i,j,k}\}))$. In this notation, index j designates a channel ('γ') variable within a view at index i and z row k, and subscript j on operator F indicates that F operates on index j only. (Operator W operates on j and k and depends upon $z_o$.) The estimates $d_{i,j}(z_o)$ are then interpolated in 'γ, for example, by a linear interpolation, to define backprojection samples where (x,y) is fixed. These estimates are then backprojected using the same backprojection operator BP(.) used above in the axial case.

The same weighting, filtering, and γ-interpolation can be applied to the samples $\{s_{i,j,k}\}$ of a derivative of line-integral function l'(z) to define a set $\{s_{i,j}(z_o)\}$ that is available at the same coordinates at which samples $\{d_{i,j}(z_o)\}$ are available.

As all these operators are linear, samples $\{s_{i,j,k}\}$ (resp. $\{s_{i,j}(z_o)\}$ represent samples of a z-derivative of a signal sampled as $\{d_{i,j,k}\}$ (resp. $\{d_{i,j}(z_o)\}$).

For illustration, assume that linear interpolation or extrapolation is applied in z to define estimates $\{d_j(z_o)\}$ for every view j. Then, without broadening a reconstructed slice width, a cubic interpolation polynomial can be defined from the four samples $\{d_{i,k1}, d_{i,k2}, s_{i,k1}, s_{i,k2}\}$, where k1, k2 pertain to $z_o$. The higher degree interpolation allows either image quality improvement if the pitch or slice aperture is kept constant, or a pitch increase or individual slice width increase. In either case, faster volume coverage is obtained at similar image quality.

In single slice scanning, availability of the z-derivative information would lead to either a pitch increase or selection of a wider slice thickness. The same is true with multislice systems. However, particular pitch selections lead to an estimation of derivative information, which are then leveraged by increasing the slice apertures (thicknesses) while retaining similar image quality. in either case, application of z-derivative information leads to increased volume coverage in a given amount of time for similar image quality.

At least one algorithm is known that defines a cubic spline interpolation polynomial from a set of irregularly spaced samples, from sample and first derivative information. in linear time, by tri-diagonal matrix inversion. A corresponding interpolation polynomial has continuous first and second derivatives.

The pitch or aperture increase limit, according to the theory, is a factor of 2, and applies to either single slice or multi-slice CT systems, as care has been taken not to restrict the set of samples used for z-interpolation.

Because projection data can normally be considered band-limited, additional information can be obtained, even when the projection data is not uniformly sampled. Thus, in one embodiment of the present invention, view-to-view resolution is improved. In both axial and step-and-shoot modes, and in cases in which a view-sampling rate is low (few projections/views per 360 degrees source rotation), equations (7) above are rewritten to give the following estimate of a derivative with respect to the source angle:

$$\frac{\partial \hat{p}}{\partial \beta} = \frac{\partial p}{\partial \gamma} - \frac{\partial Rf}{\partial t} S\cos(\gamma) \quad (9)$$

In this case, the partial derivative with respect to the fan-angle is known with a high degree of resolution $\Delta\beta >> \Delta\gamma$. In cases in which a 360-degree scan has been performed, conjugate ray data is used in accordance with the invention to obtain a precise estimate for the partial derivative of the Radon transform with respect to t.

Figure 4:
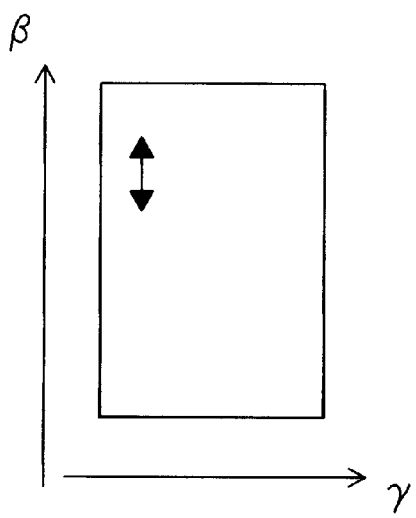
FIG. 4 is a representation of a fan beam sinogram showing interpolation/filtering along a view angle $\beta$, at a constant fan angle $\gamma$.

The rebinning process from fan beam to parallel projection data is now explained, to show how equation (9) leads, in practice, to improved azimuthal resolution. The rebinning process may naturally be decomposed or separated into to independent, sequential steps. There steps are: (1) an azimuthal, or view-to-view, rebinning interpolation; and (2) a radial, or channel-to-channel, rebinning interpolation. Starting from a fan-beam sinogram represented in FIG. 4, interpolation/filtering along β, at fan angle γ=constant, leads to a fan-parallel sinogram shown in FIG. 5. In a second step, interpolating along γ, at view angle β=constant, leads to a parallel sinogram shown in FIG. 6. View interpolation/filtering requires only a few projections to be accessed, depending upon kernel length. In one embodiment, an interpolation step is combined with a filtering step in such a manner that resolution of the data is essentially unchanged.

Figure 5:
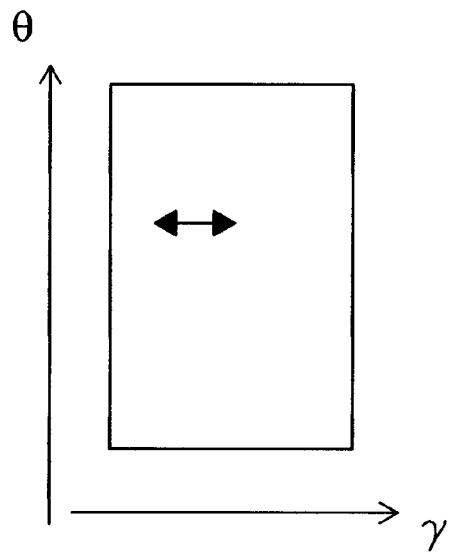
FIG. 5 is a representation of a fan beam sinogram showing interpolation/filtering along a fan angle $\gamma$, at a constant view angle $\beta$.
Figure 6:
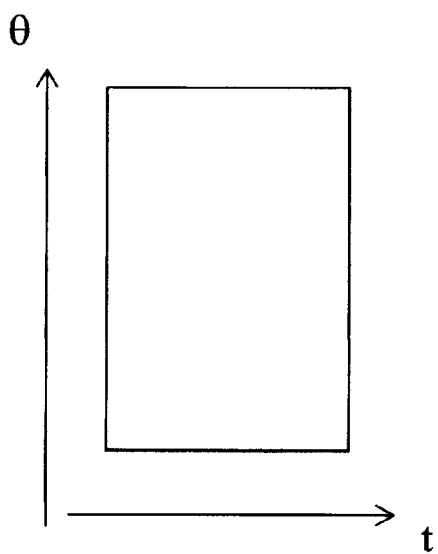
FIG. 6 is a representation of a fan beam sinogram showing axes $\theta$ and t.

After an azimuthal rebinning interpolation, channel-to-channel resolution in the sinogram of FIG. 5 is unchanged. In one embodiment, to leverage equation (9), a second interpolation step is not necessary, because equation 9 calls for evaluation of a partial Radon derivative at samples $t_i=S \sin(\gamma_i)$. By taking into account conjugate view samples, resolution along the t direction is effectively doubled, allowing a very precise numerical evaluation of a Radon partial derivative.

Reconstruction then proceeds, in one embodiment, directly from fan-beam data, after up-interpolation in a β direction to increase azimuthal resolution. This up-interpolation may be achieved, for example, by using a Hermite cubic polynomial, or by using any other interpolation method that takes into account derivative information.

Another embodiment of the invention is applicable to radial resolution in such applications as high-resolution head scanning, where a high number of views can be acquired with a stationary object, $\Delta\beta < \Delta\gamma$. An estimate of the partial derivative of the Radon transform with respect to the Radon distance t is obtained via:

$$\frac{\partial \hat{R}f}{\partial t} = \frac{1}{S\cos(\gamma)}\left\{\frac{\partial p}{\partial \gamma} - \frac{\partial p}{\partial \beta}\right\}. \quad (10)$$

Equation (10), in one embodiment, is used in conjunction with rebinning, and provides a parallel data set with improved radial (t axis) resolution. The rebinning interpolation/filtering algorithms are used to evaluate partial derivatives of p with respect to β and γ at locations called by equation (10). Conjugate ray rebinning is employed to effectively double resolution along a t axis. Combination of equation (10) with parallel reconstruction reinforces an effect of reduced radial aliasing available in parallel reconstruction as the $1/L^2$ weighting factor of the fan-beam backprojection is eliminated.

Figure 7:
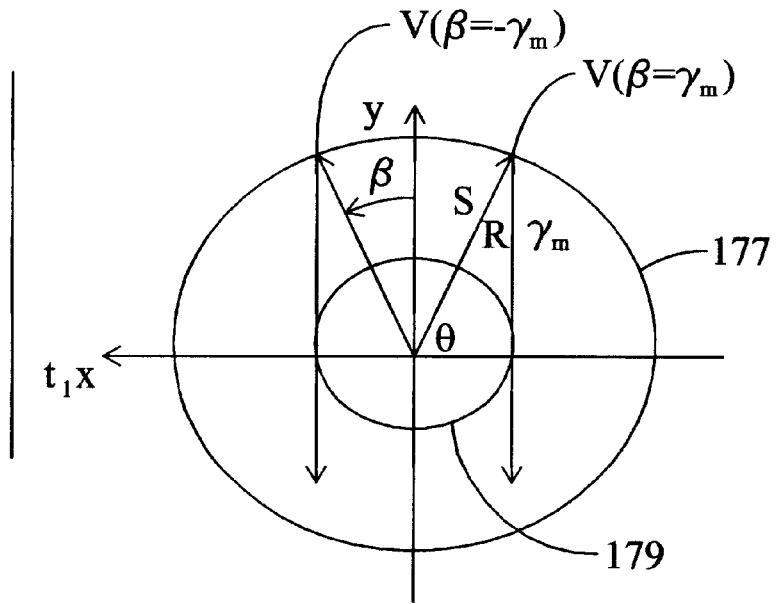
FIG. 7 is a geometric representation of a single parallel projection at angle $\theta=0$ synthesized from fan beam data.
Figure 8:
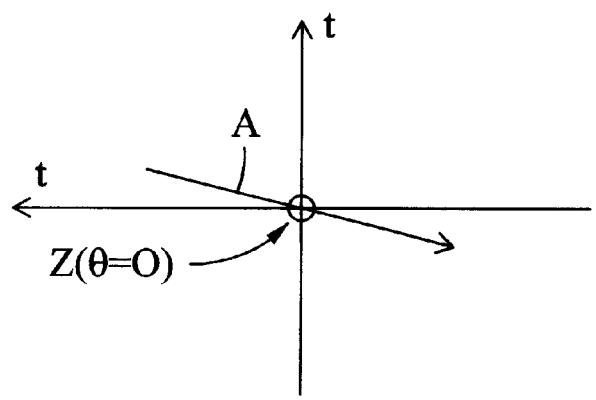
FIG. 8 is a geometric representation of Radon space sampling of FIG. 4 where a z-location of Radon samples is illustrated.
Figure 9:
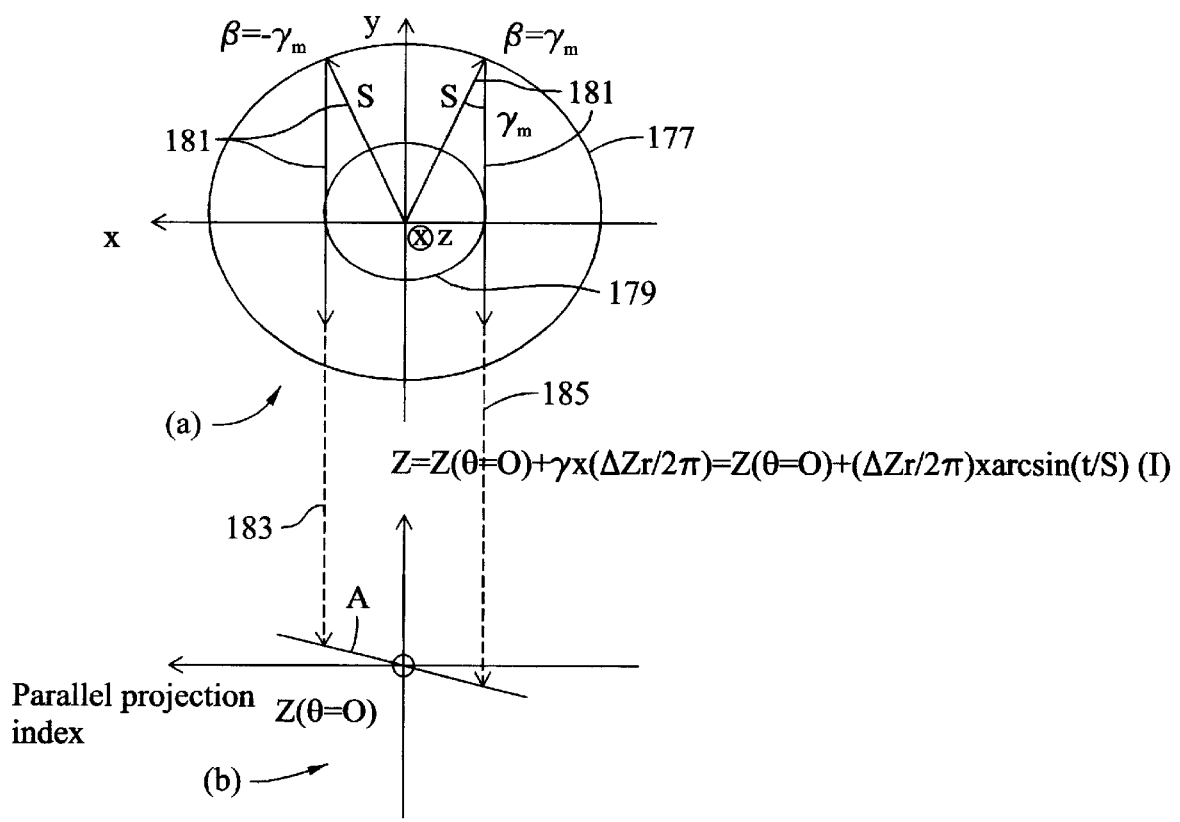
FIG. 9 is a drawing showing relationships between FIGS. 7 and 8.

In one embodiment of a single-slice helical scanner 10, in accordance with the present invention, a single projection at angle θ=0 is synthesized from the fan-beam data, as illustrated in FIG. 7. Coordinates x and y are spatial coordinates; perpendicular to both of these is a z-coordinate of CT scanner 10, which is directed into the plane of FIG. 7. Circle 177 represents a source trajectory around patient 22, and circle 179 represents a scan field of view. Radon space samples and their z-locations are indicated in FIG. 8 by a locus of points A at Z(t). Note that, in FIG. 7, θ=0, so the t axis is the same as the x axis. FIG. 9 shows more clearly the relationship of FIGS. 7 and 8. In part (a) of FIG. 9, a range of source angles $\beta, -\gamma_m \leq \beta \leq \gamma_m$, accessed to generate a single parallel projection is shown. Each ray 181 in a synthesized parallel projection is acquired at a different source angle β, and therefore a different z-location. Note that θ=β+γ, and S is a source to isocenter distance. Part (a) relates to part (b) as indicated by dashed lines 183 and 185. A z-location (with respect to a referential associated with patient table 46, assuming table translation at z-velocity>0) for a parallel projection is given by the equation in FIG. 9. The z-location is represented as a bold line A in part (b) of FIG. 9.

Figure 10:
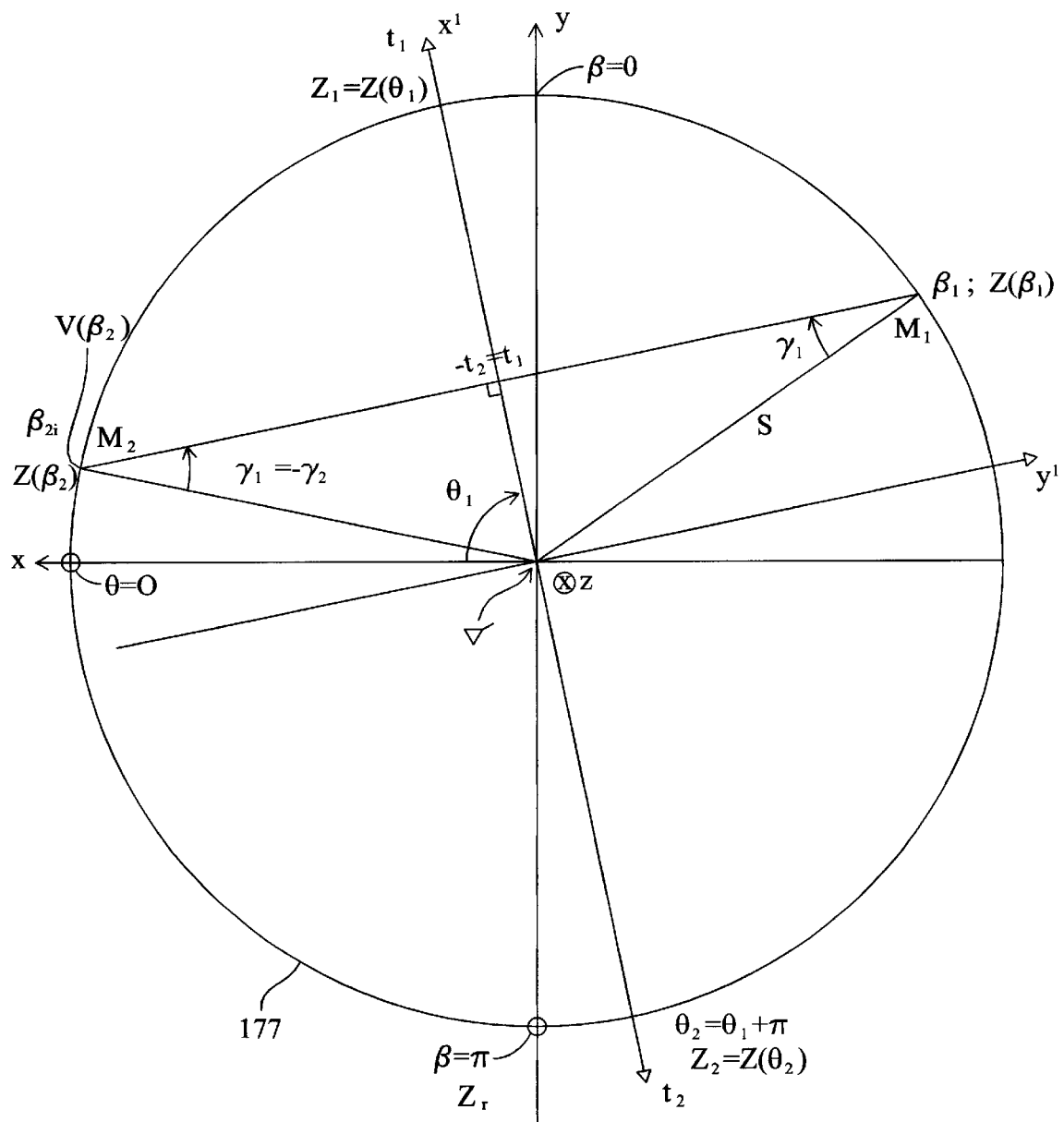
FIG. 10 is a geometric representation of parameters of a pair of conjugate measurement sampling rays in an (x,y) plane.

FIG. 10 illustrates geometry and parameters for a pair of conjugate measurements sampling the same ray in a plane (x,y). These measurements may be at different z locations, depending on a configuration of scanner 10, and possibly (in multislice scanners) at various cone angles, i.e., angles with the plane of FIG. 10. In FIG. 10, S is a source to origin, or scanner isocenter, distance. β and θ are, respectively, a source projection angle and a parallel projection angle. γ is a fan-angle. θ=β+γ when β=0 on the y axis, and θ=0 on the x axis. Angles are measured positively with respect to the direct coordinate system (x,y,z), that is, as increasing clockwise in the plane of FIG. 10. Because of the helical scanning geometry, $$z = z(\beta) = z_0 + \frac{\Delta Zr}{2\pi} \times \beta \quad (11)$$

where $z_o = z(\beta=0)$. Let $p=p(\beta,\gamma,z(\beta))$ be a measurement acquired by a single slice scanner 10 at a corresponding source and fan-angle. $Rf=Rf[t,z,\theta]$ denotes a measurement in Radon space at parallel angle $\theta$, Radon distance t from the origin, and position z with respect to object 22. Considering a single slice system and assuming source angles to be between 0 and $2\pi$, a plane of reconstruction is $z_r = z(\beta=\pi)$. Let M1 and M2 be conjugate measurements for a given ray acquired at $(\beta_1,\gamma_1)$ and $(\beta_2,\gamma_2)=(\beta_1+\pi+2\gamma_1,-\gamma_1)$. Since for conjugate rays, $\theta_2=\theta_1+\pi$, $M_1 = Rf[t_1, z(\beta_1), \theta_1]$, $M_2 = Rf[-t_1, z(\beta_1+\pi+2\gamma_1), \theta_1+\pi]$. (12)

In equations (12), angle $\theta$ is included for clarity. Let $z_1=z(\theta_1)$, and $z_2=z(\theta_2)$. M1 is written as a Taylor expansion based on the values of $Rf$ and its first derivative with respect to z at $z=z_r$, that is, in the plane of reconstruction:

$$M_1 = Rf[t_1, z_r, \theta_1] + [(z_1 - z_r) + \Delta z(t_1)]\frac{\partial Rf}{\partial z}[t_1, z_r, \theta_1] \quad (13)$$

To a second order term, the derivative of $Rf$ at $z_r$ is written as:

$$\frac{\partial Rf}{\partial z}[t_1, z_r, \theta_1] = \frac{M_2 - M_1}{z(\beta_2) - z(\beta_1)} \quad (14)$$

and:

$$\Delta z(t_1) = \frac{\Delta Zr}{2\pi}\arcsin\left(\frac{t_1}{S}\right) \quad (15)$$

Accordingly, a first estimate for the Radon sample in the plane of reconstruction is written as:

$$\hat{R}f[t_1, z_r, \theta_1] = \quad (16)$$
$$M_1 - \frac{z_1 - z_r}{z(\beta_2) - z(\beta_1)} \times (M_2 - M_1) - \Delta z(t_1)\frac{\partial Rf}{\partial z}[t_1, z_r, \theta_1]$$

Similarly a second estimate for the same sample in the plane of reconstruction is written as:

$$\hat{R}f[t_1, z_r, \theta_1] = \quad (17)$$
$$M_2 - \frac{z_2 - z_r}{z(\beta_2) - z(\beta_1)} \times (M_2 - M_1) + \Delta z(t_1)\frac{\partial Rf}{\partial z}[t_1, z_r, \theta_1]$$

By adding the two estimates for $\hat{R}f[t_1,z_r,\theta_1]$, the following is written:

$Rf[t_1, z_r, \theta_1] = T_1 \times M_1 + T_2 \times M_2$; (18)

$$T_1 = \frac{z_2 - z_r - \Delta z(t_1)}{z_2 - z_1 - 2\Delta z(t_1)};$$

$$T_2 = 1 - T_1 = \frac{z_r - z_1 - \Delta z(t_1)}{z_2 - z_1 - 2\Delta z(t_1)},$$

which is the Helical Extrapolated (HE) weighting algorithm expressed in another form. The HE weighting factor is applied to projection data and is generally based on both fan angle and view angle. Setting $\Delta z(t)=0$ leads to approximate fast-filtering algorithms.

In one embodiment of the invention, the above considerations are extended to a multi-slice scanner 10. Multi-slice scanner 10 acquires N rows, i.e., N slices, of projection data for each view angle. A pitch of scanner 10 is defined as:

$$\text{pitch} = \frac{\text{Table advance per rotation}}{\text{Slice width at isocenter}} = \frac{\Delta Zr}{s}. \quad (19)$$

Outer detector rows 18 acquire line-integral samples that are at an angle with a plane of rotation of gantry 12. This angle is known as a cone-angle, and exact image reconstruction from cone-beam data is not possible with the standard planar reconstruction algorithms. Ignoring the cone-angle leads to cone artifacts in the reconstructed images, a magnitude of which increases with the cone angle. As a partial derivative along z can be cast as a derivative with respect to the cone angle, availability of the partial derivative along z can be used to decrease the cone artifacts. There is at least one known method for three-dimensional cone-beam reconstruction based on calculation of the derivative of the Radon transform. Therefore, in one embodiment of the invention, two or more samples are acquired for a given ray in an image plane when a pitch is less than N. These relatively slow pitches lead to increased sampling per slice aperture. When a pitch is equal to N, two samples are obtained for two different source positions for a given ray in an image plane, allowing CT scanner 10 to operate with reduced current and associated increased tube life, and to provide at least two samples for helical weighting reconstruction. When a pitch is between N and 2N, some rays are sampled twice, while for others, only one source position provides a sample. In the latter case, helical weighting is done by interpolating from row to row at a given source position. Accordingly, noise and slice thickness properties of a reconstructed image vary depending upon (x,y) location. When a pitch is greater than 2N, some rays are not directly sampled, and must be estimated via extrapolation. Accordingly, image quality is degraded.

Figure 11:
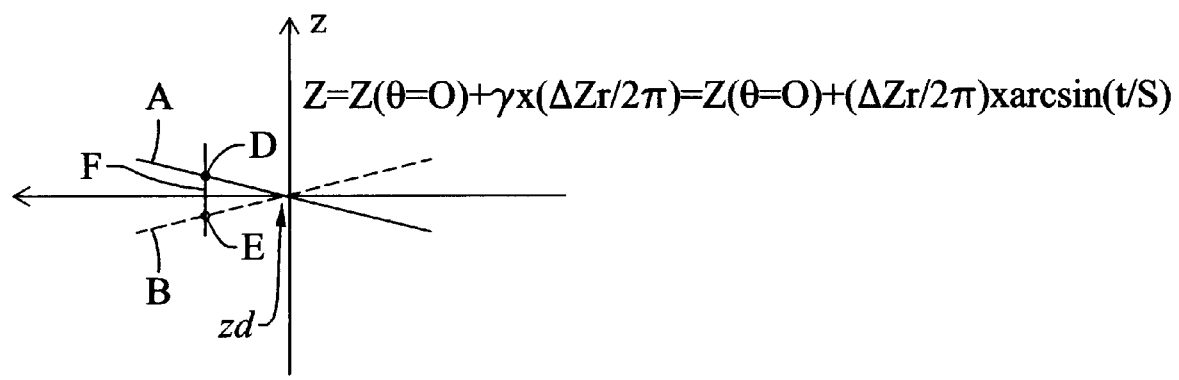
FIG. 11 is a geometric representation in Radon space of the conjugate sampling rays of FIG. 6, in which z-locations of Radon samples for direct and conjugate projections are shown.

An optimal pitch for a multirow scanner with an even number of rows is N, which provides two samples for every ray in the image plane. For a pitch of N, two conjugate rays at $\gamma=0$ are sampled by two different detector rows 18 which are at the same z-location, but which are 180° opposite one another across an isocenter O of CT scanner 10. Accordingly, $z_1=z_2=z_d(\theta)$ (which is not necessarily zero). FIG. 11 is a geometric representation of loci A and B of corresponding conjugate projections and associated Radon samples. Locus A represents a direct projection, while locus B represents a conjugate projection. The pitch in FIG. 11 is shown to be even and less than or equal to N, where N is a number of data rows or slices acquired at one source position.

Equations (16) and (17) above are rewritten as, with $z_1=z_2=z_d$:

$$\hat{R}f[t_1, z_r, \theta_1] = \tag{20}$$
$$M_1 - \frac{z_d - z_r}{z(\beta_2) - z(\beta_1)} \times (M_2 - M_1) - \Delta z(t_1) \frac{\partial Rf}{\partial z}[t_1, z_r, \theta_1]$$
$$\hat{R}f[t_1, z_r, \theta_1] =$$
$$M_2 - \frac{z_d - z_r}{z(\beta_2) - z(\beta_1)} \times (M_2 - M_1) - \Delta z(t_1) \frac{\partial Rf}{\partial z}[t_1, z_r, \theta_1]$$

From equations (20), the following equations are written:

$$Rf[t_1, z_r, \theta_1] = K_1 \times M_1 + K_2 \times M_2 \tag{21}$$

$$K_1 = \frac{1}{2}\left(1 + \frac{z_d - z_R}{z(\beta_2) - z(\beta_1)}\right) \tag{22}$$

$$K_2 = 1 - K_1 = \frac{1}{2}\left(1 - \frac{z_d - z_R}{z(\beta_2) - z(\beta_1)}\right) \tag{23}$$

$$\frac{\partial \hat{R}f}{\partial z}[t_1, z_R, \theta_1] = \frac{M_2 - M_1}{-2\Delta z(t_1)} = \frac{M_2 - M_1}{-2\frac{\Delta Z_R}{2\pi}\arcsin\left(\frac{t_1}{S}\right)} \tag{24}$$

In one embodiment of the invention, Equation (24) is used to provide an estimate of the z-derivative of the Radon transform. This estimate is used in conjunction with the sampling theorem to improve z-resolution in reconstructed images.

In another embodiment of the invention in which $z_r$ is set equal to $z_d$, equations (20) above are rewritten as:

$$\hat{R}f[t_1, z_d, \theta_1] = M_1 - \Delta z(t_1)\frac{\partial Rf}{\partial z}[t_1, z_d, \theta_1] \tag{25}$$

$$\hat{R}f[t_1, z_d, \theta_1] = M_2 + \Delta z(t_1)\frac{\partial Rf}{\partial z}[t_1, z_d, \theta_1]$$

From equations (25), the following equations are written:

$$Rf[t_1, z_d, \theta_1] = \frac{1}{2}(M_1 + M_2) \tag{26}$$

$$\frac{\partial \hat{R}f}{\partial z}[t_1, z_d, \theta_1] = \frac{M_2 - M_1}{-2\Delta z(t_1)} = \frac{M_2 - M_1}{-2\frac{\Delta Z_R}{2\pi}\arcsin\left(\frac{t_1}{S}\right)} \tag{27}$$

where equation (26) provides an alternative calculation of the Radon transform for conjugate ray sampling, and the derivative is used in conjunction with the sampling theorem to improve resolution, as in the previous embodiment.

Figure 12:
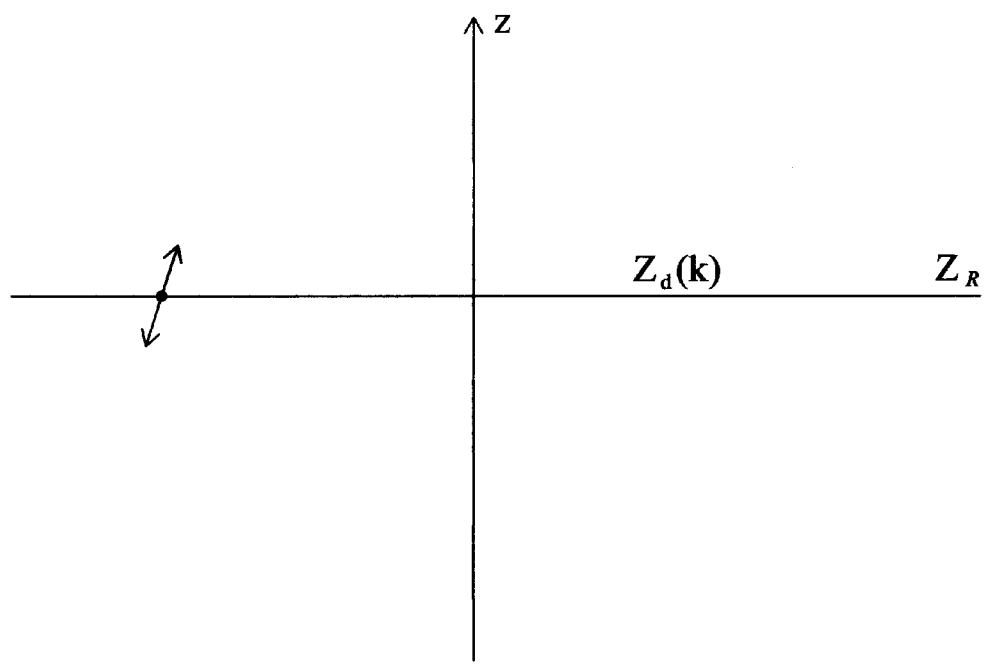
FIG. 12 is a drawing showing a representation of estimates made from a "row k" that is closest to a plane of reconstruction.

Equations (21) and (24) provide estimates of both $Rf$ and its partial derivative with respect to z directly in a plane of reconstruction. These two estimates are obtained, in one embodiment, from "row k" that is closest to the plane of reconstruction, as in FIG. 12. In another embodiment, rows "k, k+1" straddling the plane of reconstruction are used to provide two estimates for each quantity, which are then averaged to reduce noise or variations in the estimates. In particular, availability of derivative information leads to reduced partial volume via the following correction:

From a point of view of the mathematics of imaging reconstruction, direct access to the samples $R_i$ of l(z) is used, where l is a line integral through the object. However, through physics of an x-ray measurement process and subsequent logarithmic amplification, data samples $d_i$ are in a form written as:

$$R_i[\,, z_i, ] = d_i = d(z_i) = -\text{Log}(I_o) - \text{Log}\left\{\frac{1}{\Delta z}\int_{z_i - \frac{\Delta z}{2}}^{z_i + \frac{\Delta z}{2}} \exp[-l(z)]dz\right\} \tag{28}$$

where $I_o$ is the x-ray intensity impinging on the detector in the absence of an object to be imaged (air calibration).

A difference between d(z) and l(z) (known as a partial volume artifact) results in inconsistent data leading to streaks and shading in a reconstructed image, particularly in images in which a sharp edge in the line integral profile falls within the integration range. Also, the artifact shows as quantitative errors in a reconstructed density distribution.

Developing signal l(z) in a Taylor series around $z_i$, up to second order, and setting the source intensity to 1.0, the following equation is written:

$$\exp(-d_i) \approx \frac{1}{\Delta z}\int_{z_i - \frac{\Delta z}{2}}^{z_i + \frac{\Delta z}{2}} \exp\left\{-\left[l_i + (z - z_i)l'_i + \frac{(z - z_i)^2}{2}l''_i\right]\right\}dz \tag{29}$$

With:

$$\exp(x) = x + \frac{x^2}{2} \tag{30}$$

and neglecting cubic and higher order terms in $(z - z_i)$:

$$\exp(-d_i) \approx \tag{31}$$
$$\frac{\exp(-l_i)}{\Delta z}\int_{z_i - \frac{\Delta z}{2}}^{z_i + \frac{\Delta z}{2}}\left[1 - (z - z_i)l'_i + \frac{(z - z_i)}{2}((l'_i)^2 - l''_i)\right]dz,$$

leading to, after integration:

$$\exp(-d_i) = \left\{1 + \frac{[(l'_i)^2 - l''_i]}{24}\Delta z^2\right\}\exp(-l_i). \tag{32}$$

Taking the logarithm and multiplying both sides by −1, with $\text{Log}(1+x) = x$, and expressing line integral function l(z) as a function of its derivatives and of the data, $l_i$ is written as:

$$l_i \approx d_i + \frac{[(l'_i)^2 - l''_i]}{24}\Delta z^2. \tag{33}$$

The second derivative term $l''_t$ comes into play through the linear term of the exponential expansion only at the second order, and therefore corresponds exactly to the term relating the signal and its integrated version. The first derivative term corresponds to a partial volume correction.

Therefore, in one embodiment, an equation:

$$l_i \approx d_i + \frac{[(l'_i)^2 - l''_i]}{24}\Delta z^2 \tag{34}$$

further approximated by:

$$l_i \approx d_i + \frac{1}{24}(l'_i)^2 \qquad (35)$$

is obtained. This equation, together with an independent estimate of a z-derivative is used to correct "thick" slices for partial volume artifacts, and therefore obtain enhanced image quality of thinner slices while maintaining or increasing volume coverage in a given amount of time. The result is achieved by replacing $d_i$ with $Rf[,z_1,]$ and $l'_t$ with $$\frac{\partial \hat{R}f}{\partial z}[,z_i,].$$

Figure 13:
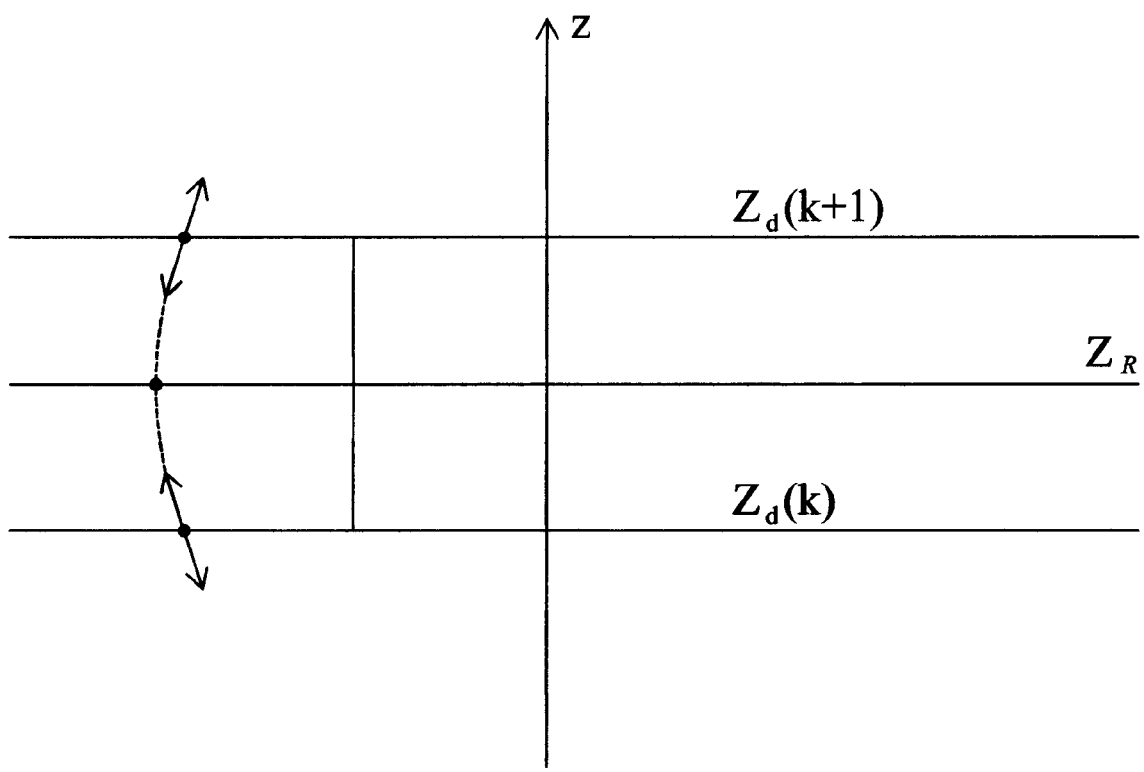
FIG. 13 is a drawing showing a representation of two estimates made from "rows k, k+1" straddling a plane of reconstruction.

In another embodiment, equations (26) and (27) are obtained by selecting $z_r = z_d$; i.e., the Radon transform and derivative information on a plane or planes $z_d(k)$ (respectively, $z_d(k+1)$) are determined. From these estimates on two planes at $z_d(k)$ and $z_d(k+1)$ represented in FIG. 13 (with k and k+1 chosen such that associated z locations are on either side of a plane of reconstruction at $z_r$), a cubic polynomial fit is defined to provide an estimate of the Radon transform on the plane of reconstruction. For example, a cubic Hermite polynomial is used for the polynomial fitting. In one embodiment, z-derivative information is also used.

It is apparent that equations (24) and (27) do not provide the derivative information for t=0 because the denominator goes to zero. This numerical difficulty at γ=0 is remedied by using a fitting of derivative information for a few adjacent channels, and using the fit to estimate a value of the derivative at t=0. Suitable fitting methods are readily available in the numerical literature.

In one embodiment of the invention, the algorithms described herein are implemented by computer 36. In another embodiment, the algorithms are implemented by image reconstructor 34. It should be understood that system 10 is described herein by way of example only, and the described algorithms can be practiced in connection with many other types of imaging systems. It will be recognized that the algorithms described herein may be implemented in many types of computing systems.

In one embodiment, for example, computer 36 executes a method for producing an enhanced tomographic image of an object in which fan beam projection data of the object is obtained in a tomographic scan, the fan beam projection data is rebinned into a quantity of parallel projection data points, interpolation sharpening is applied as part of a rebinning process to increase the quantity of parallel projection data points, and the increased quantity of parallel projection data points are used to generate a tomographic image.

In another embodiment, computer 36 applies sample and first derivative information to the parallel projection data points using a cubic spline interpolation polynomial. In another embodiment, a partial derivative of a Radon transform of an object is used to obtain and apply derivative information. In one variation, this derivative information is applied to fan-beam reconstruction to obtain higher azimuthal resolution.

In yet embodiment, partial derivatives of projection data with respect to both source and fan angles are used to obtained an estimate of a derivative of a Radon transform with respect to distance. In one variation, this derivative information is applied to parallel reconstruction to obtain improved radial resolution.

In still another embodiment, imaging system 10 is configured to produce an enhanced tomographic image of an object. The system is configured to obtain fan beam projection data of the object from fan beams of radiation in a tomographic scan, rebin the fan beam projection data into a quantity of parallel projection data points, apply interpolation to increase the quantity of parallel projection data points, and generate a tomographic image from the increased quantity of parallel projection data points.

The above described methods and apparatus provide improved resolution in CT scanning and other imaging systems. Because resolution and pitch are related, it will be recognized that the improved resolution achievable in accordance with the present invention can be traded, in single-slice and multiple slice CT scanners, for an increased pitch, thereby increasing scanning efficiency and speed. For view-to-view axial improvement in either single or multi-slice systems, operated in axial (step and shoot) or helical modes, embodiments of the present invention do not require a full rebinning, and can be leveraged directly in a framework of fan-beam reconstruction. The same advantages apply to embodiments providing radial resolution improvement. For example, rebinning and parallel reconstruction are used for aliasing cancellation via quarter offset and rebinning, together with radial resolution improvement given by equation (10). Embodiments in which z-derivative information is independently available are applicable to signal and multi-slice systems, and helical and axial scanning. Where z-derivative information is not independently available, an embodiment provides methods for estimating the z-derivative information directly, for multislice systems used in helical mode at specific pitches.

Although the invention has been described and illustrated in detail, it is to be clearly understood that the same is intended by way of illustration and example only and is not to be taken by way of limitation. After having read and understood the various embodiments presented by way of illustration here, many variations within the spirit and scope of the present invention will become evident to those skilled in the art. Accordingly, the spirit and scope of the present invention are to be limited only by the terms of the appended claims and their equivalents.

What is claimed is:

1. A method for producing an enhanced tomographic image of an object, said method comprising:

obtaining fan beam projection data of the object from a tomographic scan;

rebinning the fan beam projection data into a quantity of parallel projection data points;

applying interpolation to the quantity of parallel projection data points to increase the quantity of parallel projection data points, wherein applying interpolation to increase the quantity of parallel projection data points comprises applying derivative information to reduce a data sampling interval;

generating a tomographic image from the increased quantity of parallel projection data points; and determining a partial derivative of a Radon transform of the parallel projection data points to generate the applied derivative information.

2. A method in accordance with claim 1 wherein applying interpolation to increase the quantity of parallel projection data points further comprises estimating partial derivatives of the fan beam projection data with respect to a source angle using partial derivatives of the fan beam projection data with respect to a fan angle and partial derivatives of the Radon transform of the parallel projection data points with respect to a Radon distance coordinate.

3. A method in accordance with claim 2 wherein estimating partial derivatives of the fan beam projection data with respect to a source angle from partial derivatives of the fan beam projection data with respect to a fan angle and partial derivatives of the Radon transform of the parallel projection data points with respect to a Radon distance coordinate comprises determining an estimate $$\frac{\partial \hat{p}}{\partial \beta}$$

as:

$$\frac{\partial \hat{p}}{\partial \beta} = \frac{\partial p}{\partial \gamma} - \frac{\partial Rf}{\partial t} S\cos(\gamma),$$

where:
 p=p($\beta$,$\gamma$,k) denotes fan beam projection data;
 k is a row (slice) index;
 $\beta$ is a projection angle;
 $\gamma$ is a ray angle (fan angle);
 t=S sin($\gamma$) is a Radon distance coordinate;
 Rƒ=Rƒ($\theta$,t,z) is a Radon transform of parallel projection data points;
 $\theta$=$\beta$+$\gamma$, $$z = z_0 + kx\Delta Z_S + \left(\frac{\beta}{2\pi}\right)x\Delta Z_S;$$

$\Delta Z_S$ is a slice aperture;
 $\Delta Z_R$ is a table advance per 2 $\pi$ rotation of a radiation source; and
 S is a distance from a vertex of the radiation source to a scanner isocenter.

4. A method in accordance with claim 1 wherein applying interpolation to increase the quantity of parallel projection data points further comprises estimating partial derivatives of the Radon transform of the parallel projection data points with respect to a Radon distance coordinate using partial derivatives of the fan beam projection data with respect to a fan angle and partial derivatives of the fan beam projection data with respect to a projection angle.

5. A method in accordance with claim 4 wherein estimating partial derivatives of the Radon transform of the parallel projection data points with respect to a Radon distance coordinate using partial derivatives of the fan beam projection data with respect to a fan angle and partial derivatives of the fan beam projection data with respect to a projection angle comprises:

determining an estimate $$\frac{\partial \hat{R}f}{\partial t}$$

as:

$$\frac{\partial \hat{R}f}{\partial t} = \frac{1}{S\cos(\gamma)}\left\{\frac{\partial p}{\partial \gamma} - \frac{\partial p}{\partial \beta}\right\}$$

where:
 p=p($\beta$,$\gamma$,k) denotes fan beam projection data;
 k is a row (slice) index;
 $\beta$ is a projection angle;
 $\gamma$ is a ray angle (fan angle);
 t=S sin($\gamma$) is a Radon distance coordinate;
 Rƒ=Rƒ($\theta$,t,z) is a Radon transform of parallel projection data points;
 $\theta$=$\beta$+$\gamma$, $$z = z_0 + kx\Delta Z_S + \left(\frac{\beta}{2\pi}\right)x\Delta Z_S;$$

$\Delta Z_S$ is a slice aperture;
 $\Delta Z_R$ is a table advance per 2 $\pi$ rotation of a radiation source; and
 S is a distance from a vertex of the radiation source to a scanner isocenter.

6. A method in accordance with claim 1 wherein obtaining fan beam projection data of the object from fan beams of radiation in a tomographic scan comprises the step of obtaining conjugate ray measurements of fan beam projection data.

7. A method in accordance with claim 6 wherein rebinning the fan beam projection data into parallel projection data points comprises determining a Radon transform of the fan beam projection data.

8. A method in accordance with claim 7 wherein applying derivative information to reduce a data sampling interval comprises determining estimates of a partial derivative of a Radon transform of the parallel projection data points with respect to z, where z is a distance in a direction perpendicular to a scanning plane of the fan beam of radiation.

9. A method in accordance with claim 8 wherein determining estimates of a partial derivative of a Radon transform of the parallel projection data points with respect to z comprises the step of determining:

$$\frac{\partial \hat{R}f}{\partial z}[t_1, z_R, \theta_1] = \frac{M_2 - M_1}{-2\Delta z(t_1)} = \frac{M_2 - M_1}{2\frac{\Delta Z_R}{2\pi}\arcsin\left(\frac{t_1}{S}\right)}$$

where:

$$\frac{\partial \hat{R}f}{\partial z}[t_1, z_R, \theta_1]$$

is an estimate of a partial derivative of a Radon transform of the parallel projection data points with respect to z at t=$t_1$, z=$z_R$, $\theta$=$\theta_1$;
 $M_1$ and $M_2$ are conjugate measurements for a given ray acquired at ($\beta_1$,$\gamma_1$) and ($\beta_2$,$\gamma_2$)=($\beta_1$+$\pi$−2 $\gamma_1$, −$\gamma_1$), respectively;
 $\beta_1$ and $\beta_2$ are source projection angles;
 $\gamma_1$ and $\gamma_2$ are fan angles;
 t is a Radon distance coordinate;

$z_R$ is a value of z for a source projection angle $\beta=\pi$, $\theta$ is a parallel projection angle;

S is a distance from a vertex of a radiation source to a scanner isocenter; and $\Delta Z_R$ is a table advance per $2\pi$ rotation of the radiation source.

10. A method in accordance with claim 9 further comprising the step of utilizing an approximation written as:

$$l_i \approx d_i + \frac{[(l_i')^2 - l_i'']}{24}\Delta z^2$$

together with an independent estimate of a z-derivative to correct "thick" slices for partial volume artifacts, wherein:

$$R_f[\,, z_i,] =$$

$$d_i = d(z_i) = -\text{Log}(I_o) - \text{Log}\left\{\frac{1}{\Delta z}\int_{z_1-\frac{\Delta z}{2}}^{z_1+\frac{\Delta z}{2}} \exp[-l(z)]dz\right\}$$

where $I_o$ is an x-ray intensity of a radiation beam impinging on a radiation detector in the absence of an object to be imaged.

11. A method in accordance with claim 9 further comprising the step of utilizing an approximation written as:

$$l_i \approx d_i + \frac{1}{24}(l_i')^2$$

together with an independent estimate of a z-derivative to correct "thick" slices for partial volume artifacts, wherein:

$$R_f[\,, z,] =$$

$$d_i = d(z_i) = -\text{Log}(I_o) - \text{Log}\left\{\frac{1}{\Delta z}\int_{z_1-\frac{\Delta z}{2}}^{z_1+\frac{\Delta z}{2}} \exp[-l(z)]dz\right\}$$

where $I_o$ is an x-ray intensity of a radiation beam impinging on a radiation detector in the absence of an object to be imaged.

12. A method in accordance with claim 9 wherein determining a Radon transform of the fan beam projection data comprises determining a Radon transform $$Rf[t_1, z_R, \theta_1] = K_1 \times M_1 + K_2 \times M_2;$$

where:

$$K_1 = \frac{1}{2}\left(1 + \frac{z_d - z_R}{z(\beta_2) - z(\beta_1)}\right);$$

$K_2 = 1 - K_1;$ $z_d$ is a value of z at which the conjugate rays cross; and $z(\beta_1)$ and $z(\beta_2)$ are values of z for source projection angles $\beta_1$ and $\beta_2$, respectively.

13. A method in accordance with claim 12 wherein $z_d = z_R$.

14. A system for producing an enhanced tomographic image of an object, said system configured to:

obtain fan beam projection data of the object from fan beams of radiation in a tomographic scan;

rebin the fan beam projection data into a quantity of parallel projection data points;

apply interpolation to the quantity of parallel projection data points to increase the quantity of parallel projection data points;

apply derivative information in applying interpolation, thereby reducing a data sampling interval;

generate a tomographic image from the increased number of parallel projection data points; and determine a partial derivative of a Radon transform of the parallel projection data points to generate the applied derivative information.

15. A system in accordance with claim 14 further configured to apply interpolation by determining estimates of partial derivatives of the fan beam projection data with respect to a source angle using partial derivatives of the fan beam projection data with respect to a fan angle and partial derivatives of the Radon transform of the parallel projection data points with respect to a Radon distance coordinate.

16. A system in accordance with claim 15 configured to determine an estimate $$\frac{\partial \hat{p}}{\partial \beta}$$

as:

$$\frac{\partial \hat{p}}{\partial \beta} = \frac{\partial p}{\partial \gamma} - \frac{\partial Rf}{\partial t}S\cos(\gamma),$$

where:

$p = p(\beta, \gamma, k)$ denotes fan beam projection data;

k is a row (slice) index;

$\beta$ is a projection angle;

$\gamma$ is a ray angle (fan angle);

$t = S\sin(\gamma)$ is a Radon distance coordinate;

$Rf = Rf(\theta, t, z)$ is a Radon transform of parallel projection data points;

$\theta = \beta + \gamma,$ $$z = z_0 + kx\Delta Zs + \left(\frac{\beta}{2\pi}\right)lx\Delta Zs;$$

$\Delta Zs$ is a slice aperture;

$\Delta Z_R$ is a table advance per $2\pi$ rotation of a radiation source; and

S is a distance from a vertex of the radiation source to a scanner isocenter.

17. A system in accordance with claim 14 further configured to apply interpolation by estimating partial derivatives of the Radon transform of the parallel projection data points with respect to a Radon distance coordinate using partial derivatives of the fan beam projection data with respect to a fan angle and partial derivatives of the fan beam projection data with respect to a projection angle.

18. A system in accordance with claim 17 configured to determine an estimate $$\frac{\partial \hat{R}f}{\partial t}$$

as:

$$\frac{\partial \hat{R}f}{\partial t} = \frac{1}{S\cos(\gamma)}\left\{\frac{\partial p}{\partial \gamma} - \frac{\partial p}{\partial \beta}\right\}$$

where:
$p = p(\beta,\gamma,k)$ denotes fan beam projection data;
k is a row (slice) index;
$\beta$ is a projection angle;
$\gamma$ is a ray angle (fan angle);
$t = S \sin(\gamma)$ is a Radon distance coordinate;
$Rf = Rf(\theta,t,z)$ is a Radon transform of parallel projection data points;
$\theta = \beta + \gamma$, $$z = z_0 + kx\Delta Zs + \left(\frac{\beta}{2\pi}\right)x\Delta Zs;$$

$\Delta Zs$ is a slice aperture;
$\Delta Z_R$ is a table advance per $2\pi$ rotation of a radiation source; and
S is a distance from a vertex of the radiation source to a scanner isocenter.

19. A system in accordance with claim 14 configured to obtain conjugate ray measurements of fan beam projection data.

20. A system in accordance with claim 19 configured to rebin the fan beam projection data by determining a Radon transform of the fan beam projection data.

21. A system in accordance with claim 20 configured to apply derivative information by determining estimates of a partial derivative of a Radon transform of the parallel projection data points with respect to z, where z is a distance in a direction perpendicular to a scanning plane of the fan beam of radiation.

22. A system in accordance with claim 21 configured to determine estimates of a partial derivative of a Radon transform of the parallel projection data points with respect to z by determining:

$$\frac{\partial \hat{R}f}{\partial z}[t_1, z_R, \theta_1] = \frac{M_2 - M_1}{-2\Delta z(t_1)} = \frac{M_2 - M_1}{2\frac{\Delta Z_R}{2\pi}\arcsin\left(\frac{t_1}{S}\right)}$$

where:

$$\frac{\partial \hat{R}f}{\partial z}[t_1, z_R, \theta_1]$$

is an estimate of a partial derivative of a Radon transform of the parallel projection data points with respect to z at $t = t_1$, $z = z_R$, $\theta = \theta_1$;
$M_1$ and $M_2$ are conjugate measurements for a given ray acquired at $\beta_1$, $\gamma_1$) and $(\beta_2, \gamma_2) = (\beta_1 + \pi - 2\gamma_1, \gamma_1)$, respectively;
$\beta_1$ and $\beta_2$ are source projection angles;

$\gamma_1$ and $\gamma_2$ are fan angles;
t is a Radon distance coordinate;
$z_R$ is a value of z for a source projection angle $\beta = \pi$,
$\theta$ is a parallel projection angle;
S is a distance from a vertex of a radiation source to a scanner isocenter; and
$\Delta Z_R$ is a table advance per $2\pi$ rotation of the radiation source.

23. A system in accordance with claim 22 further comprising the step of utilizing an approximation written as:

$$l_i \approx d_i + \frac{[(l_i')^2 - l_i'']}{24}\Delta z^2$$

together with an independent estimate of a z-derivative to correct "thick" slices for partial volume artifacts, wherein:

$R_f[, z_i,] =$ $$d_i = d(z_i) = -\text{Log}(I_o) - \text{Log}\left\{\frac{1}{\Delta z}\int_{z_i-\frac{\Delta z}{2}}^{z_i+\frac{\Delta z}{2}} \exp[-l(z)]dz\right\}$$

where $I_o$ is an x-ray intensity of a radiation beam impinging on a radiation detector in the absence of an object to be imaged.

24. A system in accordance with claim 22 further comprising the step of utilizing an approximation written as:

$$l_i \approx d_i + \frac{1}{24}(l_i')^2$$

together with an independent estimate of a z-derivative to correct "thick" slices for partial volume artifacts, wherein:

$R_f[, z_i,] =$ $$d_i = d(z_i) = -\text{Log}(I_o) - \text{Log}\left\{\frac{1}{\Delta z}\int_{z_i-\frac{\Delta z}{2}}^{z_i+\frac{\Delta z}{2}} \exp[-l(z)]dz\right\}$$

where $I_o$ is an x-ray intensity of a radiation beam impinging on a radiation detector in the absence of an object to be imaged.

25. A system in accordance with claim 22 configured to determine a Radon transform of the fan beam projection data by determining a Radon transform $$Rf[t_1,z_R,\theta_1] = K_1 \times M_1 + K_2 \times M_2;$$

where:

$$K_1 = \frac{1}{2}\left(1 + \frac{z_d - z_R}{z(\beta_2) - z(\beta_1)}\right);$$

$K_2 = 1 - K_1$;
$z_d$ is a value of z at which the conjugate rays cross; and
$z(\beta_1)$ and $z(\beta_2)$ are values of z for source projection angles $\beta_1$ and $\beta_2$, respectively.

26. A system in accordance with claim 25 wherein $z_d = z_r$.

* * * * *

UNITED STATES PATENT AND TRADEMARK OFFICE
CERTIFICATE OF CORRECTION

PATENT NO. : 6,411,670 B1
DATED : June 25, 2002
INVENTOR(S) : Guy M. Besson

It is certified that error appears in the above-identified patent and that said Letters Patent is hereby corrected as shown below:

Column 17,
Lines 20 and 40, delete "$z_1 + \frac{\Delta z}{2}$" insert therefor -- $z_i + \frac{\Delta z}{2}$ --.

Lines 20 and 40, delete "$z_1 - \frac{\Delta z}{2}$" insert therefor -- $z_i - \frac{\Delta z}{2}$ --.

Column 19,
Line 65, delete "$\beta_1, \gamma_1$)" insert therefor -- ($\beta_1, \gamma_1$)" --.

Signed and Sealed this

Sixteenth Day of December, 2003

JAMES E. ROGAN
*Director of the United States Patent and Trademark Office*